United States Patent [19]

Gers-Barlag et al.

[11] Patent Number: 6,022,530

[45] Date of Patent: Feb. 8, 2000

[54] STABLE COSMETIC AND DERMATOLOGICAL LIGHT-PROTECTING PREPARATIONS IN THE FORM OF WATER/OIL EMULSIONS CONTAINING INORGANIC MICRO-PIGMENTS, DERIVATIVES OF TRIAZINE AND/OR OTHER COMPONENTS

[75] Inventors: Heinrich Gers-Barlag; Albrecht Dörschner; Rainer Kröpke; Anja Müller; Bente Nissen; Arianne Schomann, all of Hamburg, Germany

[73] Assignee: Beiersdorf AG, Hamburg, Germany

[21] Appl. No.: 09/101,788

[22] PCT Filed: Jan. 17, 1997

[86] PCT No.: PCT/EP97/00217

§ 371 Date: Nov. 27, 1998

§ 102(e) Date: Nov. 27, 1998

[87] PCT Pub. No.: WO97/26857

PCT Pub. Date: Jul. 31, 1997

[30] Foreign Application Priority Data

Jan. 25, 1996 [DE] Germany .................. 196 02 619

[51] Int. Cl.$^7$ .................. A61K 7/42; A61K 7/44; A61K 7/00

[52] U.S. Cl. .................. 424/59; 424/60; 424/400; 424/401; 574/937; 574/938

[58] Field of Search .................. 424/89, 60, 400, 424/401; 514/937, 938

[56] References Cited

U.S. PATENT DOCUMENTS 4,454,113 6/1984 Hemker .

FOREIGN PATENT DOCUMENTS 457687 11/1991 European Pat. Off. .

OTHER PUBLICATIONS

Seifen, Ole, Fette, Wachse, Bd. 115, Nr. 18, pp. 661–662, K. Sperling: "UV filter . . . Formulierungen".

Database WPI, Week 9233, Derwent Publications Ltd., London, G.B., AN 92–272108, "Emulsified cosmetic . . . water", & JP 04 178 316 A (KAO), Jun. 25, 1992.

Primary Examiner—Shelley A. Dodson
Attorney, Agent, or Firm—Sprung Kramer Schaefer & Briscoe

[57] ABSTRACT

Cosmetic or dermatological light protection formulations in the form of W/O emulsions, comprising (a) one or more light protection filter substances which are solid under normal conditions and (b) one or more W/O emulsifiers chosen from the group of substances of the general structural formula

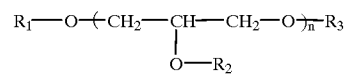

in which $R_1$, $R_2$ and $R_3$ independently of one another are chosen from the group which consists of: H, branched or unbranched, saturated or unsaturated fatty acid radicals having from 8 to 24 carbon atoms, in which up to 3 aliphatic hydrogen atoms may be substituted by hydroxyl groups, and n is a number from 2 to 8.

7 Claims, No Drawings

STABLE COSMETIC AND DERMATOLOGICAL LIGHT-PROTECTING PREPARATIONS IN THE FORM OF WATER/OIL EMULSIONS CONTAINING INORGANIC MICRO-PIGMENTS, DERIVATIVES OF TRIAZINE AND/OR OTHER COMPONENTS

The present invention relates to cosmetic and dermatological light protection formulations, in particular skincare cosmetic and dermatological light protection formulations.

The damaging effect of the ultraviolet part of solar radiation on the skin is generally known. While rays having a wavelength of less than 290 nm (the UVC region) are absorbed by the ozone layer in the Earth's atmosphere, rays in the region between 290 nm and 320 nm, the UVB region, cause erythema, simple sunburn or even burns of varying severity.

The narrower region around 308 nm is stated as the erythema activity maximum of sunlight.

Numerous compounds are known for protecting against UVB radiation; these are usually derivatives of 3-benzylidenecamphor, 4-aminobenzoic acid, cinnamic acid, salicylic acid, benzophenone and also 2-phenylbenzimidazole.

For the region between about 320 nm and about 400 nm, the UVA region, it is also important to have available filter substances, since the rays of that region can also cause damage. Thus, it has been found that UVA radiation leads to damage of the elastic and collagenic fibres of connective tissue, causing premature ageing of the skin, and that it is to be regarded as a cause of numerous phototoxic and photo-allergic reactions. The damaging effect of UVB radiation can be intensified by UVA radiation.

However, UV radiation can also lead to photochemical reactions, in which case the photochemical reaction products intervene in the skin's metabolism.

Such photochemical reaction products are predominantly free-radical compounds, for example hydroxyl radicals. Undefined free-radical photo-products which are formed in the skin itself can also display uncontrolled secondary reactions because of their high reactivity. However, singlet oxygen, a non-radical excited state of the oxygen molecule, can also be formed during UV irradiation, as can short-lived epoxides and many others. Singlet oxygen, for example, differs from the normal triplet oxygen (free-radical ground state) by its increased reactivity. However, excited, reactive (free-radical) triplet states of the oxygen molecule also exist.

UV radiation is also a type of ionizing radiation. There is therefore the risk that UV exposure may also produce ionic species, which then, for their part, are capable of oxidative intervention in the biochemical processes.

An advantageous UVB filter is tris(2-ethylhexyl) 4,4',4''-(1,3,5-triazine-2,4,6-triyltriimino)trisbenzoate, synonym: 2,4,6-tris[anilino-(p-carbo-2'-ethyl-1'-hexyloxy)]-1,3,5-triazine.

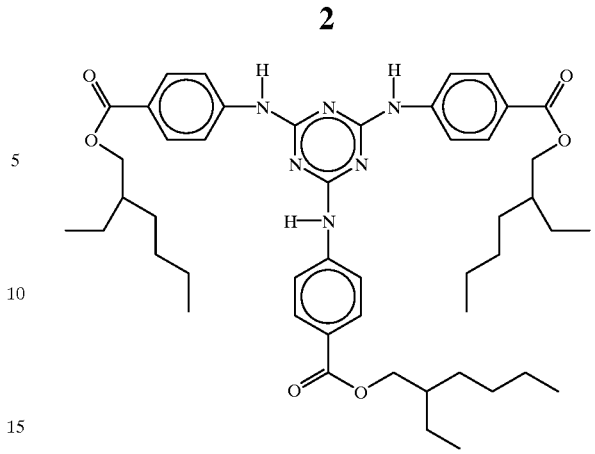

This UVB filter substance is marketed by BASF Aktiengesellschaft under the trade name UVINUL° T 150 and is distinguished by good UV absorption properties.

The main disadvantage of this UVB filter is its poor solubility in lipids. Known solvents for this UVB filter can dissolve a maximum of about 15% by weight of this filter, corresponding to about 1–1.5% by weight of dissolved, and thus active, UV filter substance.

UV absorbers or UV reflectors are most inorganic pigments, which are used in a known manner in cosmetics for protecting the skin against UV rays. Said inorganic pigments are oxides of titanium, zinc, iron, zirconium, silicon, manganese, aluminium and cerium and mixtures thereof, as well as modifications.

Inorganic pigments are notable per se for their good photoprotective effect. They do, however, have the disadvantage that it is difficult to incorporate them satisfactorily into such formulations. Only when the particles in the final formulation are very small are they not observed to produce a disturbing "whitening" (formation of white spots on the skin) following application to the skin. The particle sizes of such pigments are usually in the range below 100 nm. In a conventional emulsion the particles tend, to a greater or lesser extent, to combine to form agglomerates which are visible even under the light microscope. Moreover, such agglomeration does not end with the manufacturing process of a corresponding formulation, but continues during storage. The "whitening" can therefore increase further over a prolonged period of time. In the medium or long term, this type of agglomeration can also lead to oil loss or even emulsion breakdown.

A further disadvantage of using inorganic pigments in cosmetic formulations is that such pigments lead to severe dryness of the skin in the vast majority of cases.

In addition, known and customary light protection filter substances are 4-(tert-butyl)-4'-methoxydibenzoylmethane, which is characterized by the structure

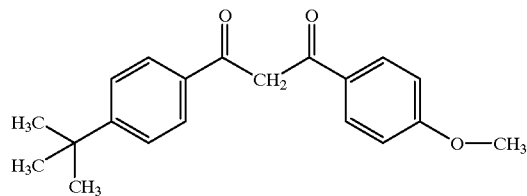

and marketed by Givaudan under the trade name Parsol®
1789, and 4-methylbenzylidenecamphor, which is characterized by the structure

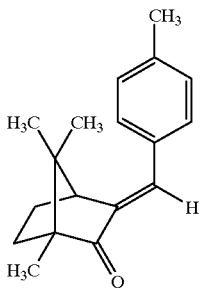

and is marketed by Merck under the trade name Eusolex®
6300. These substances are notable per se for good UV filter
properties. In combination with one another or with other
substances in solid form, their use concentration is, however,
limited.

Particularly if two or more of the light protection substances which are solid under normal conditions are present, for example chosen from the group tris(2-ethylhexyl) 4,4', 4"-(1,3,5-triazine-2,4, 6-triyltriimino)trisbenzoate, 4-methylbenzylidenecamphor, 4-(tert-butyl)-4'-methoxydibenzoylmethane and titanium dioxide, in accordance with the prior art, only low use concentrations in each case and thus only low light protection factors are possible unless the oil phase proportion is increased disproportionately, which would, however, likewise have disadvantages.

Nevertheless, the disadvantage of the prior art was that normally either only comparatively low light protection factors could be achieved, or that the light protection filters had an insufficient UV stability or inadequate physiological compatibility or insufficiently high solubility or dispersibility in cosmetic or dermatological formulations, or exhibited other incompatibilities with cosmetic or dermatological formulations, or had several disadvantages at the same time.

To overcome at least some, if not all, of these disadvantages was an object of the present invention.

It was therefore surprising, and could not have been foreseen by the person skilled in the art, that cosmetic or dermatological light protection formulations in the form of W/O emulsions, comprising
 (a) one or more light protection filter substances which are solid under normal conditions and
 (b) one or more W/O emulsifiers chosen from the group of substances of the general structural formula

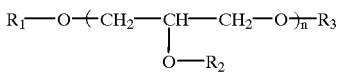

in which $R_1$, $R_2$ and $R_3$ independently of one another are selected from the group which consists of: H, branched or unbranched, saturated or unsaturated fatty acid radicals having from 8 to 24 carbon atoms, in which up to 3 aliphatic hydrogen atoms may be substituted by hydroxyl groups, and n is a number from 2 to 8, overcome the disadvantages of the prior art.

An advantageous embodiment of the present invention comprises cosmetic or dermatological light protection formulations in the form of W/O emulsions comprising
 (a) one or more light protection filter substances which are solid under normal conditions, chosen from the group consisting of tris(2-ethylhexyl) 4,4',4"-(1,3,5-triazine-2,4,6-triyltriimino)trisbenzoate, 4-methylbenzylidenecamphor, 4-(tert-butyl)-4'-methoxydibenzoylmethane, inorganic micropigments, in particular hydrophobicized inorganic micropigments, and
 (b) one or more W/O emulsifiers chosen from the group of substances of the general structural formula

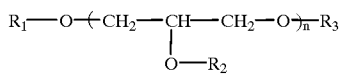

in which $R_1$, $R_2$ and $R_3$ independently of one another are chosen from the group which consists of: H, branched or unbranched, saturated or unsaturated fatty acid radicals having from 8 to 24 carbon atoms, in which up to 3 aliphatic hydrogen atoms may be substituted by hydroxyl groups, and n is a number from 2 to 8.

A particularly advantageous embodiment of the present invention comprises cosmetic or dermatological light protection formulations in the form of W/O emulsions comprising
 (a) tris(2-ethylhexyl) 4,4',4"-(1,3,5-triazine-2,4,6-triyltriimino)trisbenzoate, 4-methylbenzylidenecamphor, 4-(tert-butyl)-4'-methoxydibenzoylmethane and hydrophobicized titanium dioxide as inorganic micropigment, and
 (b) one or more W/O emulsifiers chosen from the group of substances of the general structural formula

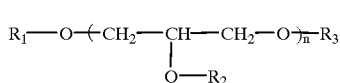

in which $R_1$, $R_2$ and $R_3$ independently of one another are chosen from the group which consists of: H, branched or unbranched, saturated or unsaturated fatty acid radicals having from 8 to 24 carbon atoms, in which up to 3 aliphatic hydrogen atoms may be substituted by hydroxyl groups, and n is a number from 2 to 8.

The emulsifier "polyglyceryl-2 polyhydroxystearate" has proven very particularly advantageous; it is filed under the registry numbers 156531-21-4 and 144470-58-6 in the "Chemical Abstracts", and is available, for example, under the trade name DEHYMULS® PGPH from Henkel KGaA.

JP-Hei-04/178316 does describe cosmetic formulations containing emulsifiers which fall under the structural formula given under (b), although there is no indication of the present invention therein.

In the active ingredient combinations according to the invention and in cosmetic or dermatological formulations comprising these active ingredient combinations, even the less soluble components have better solubility than in the prior art formulations, even if two or more such components are present.

According to the invention, it is also possible to prevent agglomeration of any inorganic pigment particles which may be present (which are of course present in dispersed, and not dissolved, form) and consequential "whitening", oil loss and emulsion breakdown, even if one or more less soluble components are additionally present.

Furthermore, light protection formulations according to the invention are obtainable which have greater stability, in particular stability against decomposition under the influence of light, very particularly UV light, than the prior art would have suggested. In addition, formulations which are particularly well tolerated by the skin are obtainable according to the invention.

A prerequisite for the suitability of the active ingredient combinations according to the invention for the purposes according to the invention is of course the cosmetic or dermatological acceptability of the base substances.

According to the invention, it is possible to increase significantly, compared with the prior art, the use amounts of tris(2-ethylhexyl) 4,4',4"-(1,3,5-triazine-2,4,6-triyltriimino) trisbenzoate, but also of the other light protection filter substances which are solid under normal conditions, in cosmetic or dermatological formulations.

It was also surprising that the addition of emulsifiers used according to the invention and 4-(tert-butyl)-4'-methoxydibenzoylmethane and/or 4-methylbenzylidenecamphor has a stabilizing effect on solutions of tris(2-ethylhexyl) 4,4',4"-(1,3,5-triazine-2,4,6-triyltriimino)trisbenzoate, since the latter substance not only has poor solubility, but also readily recrystallizes from its solution. The invention thus also relates to a process for stabilizing solutions of tris(2-ethylhexyl) 4,4',4"-(1,3,5-triazine-2,4,6-triyltriimino)trisbenzoate, which is characterized in that an effective content of one or more emulsifiers used according to the invention and 4-(tert-butyl)-4'-methoxydibenzoylmethane and/or 4-methylbenzylidenecamphor is added to such solutions.

It was further surprising that the UV stability of UV filter substances used individually, in particular 4-(tert-butyl)-4'-methoxydibenzoylmethane, can be increased considerably according to the invention.

The total amount of tris(2-ethylhexyl) 4,4',4"-(1,3,5-triazine-2,4,6-triyltriimino)trisbenzoate in the finished cosmetic or dermatological formulations is advantageously chosen from the range 0.1–10.0% by weight, preferably 0.5–6.0% by weight, based on the total weight of the formulations.

The total amount of 4-(tert-butyl)-4'-methoxydibenzoylmethane and/or 4-methylbenzylidenecamphor in the finished cosmetic or dermatological formulations is advantageously chosen from the range 0.1–10.0% by weight, preferably 0.5–6.0% by weight, based on the total weight of the formulations.

The total amount of emulsifier(s) according to the invention in the finished cosmetic or dermatological formulations is advantageously chosen from the range 0.1–25.0% by weight, preferably 0.5–6.0% by weight, based on the total weight of the formulations.

Cosmetic and dermatological formulations according to the invention also comprise inorganic pigments based on metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$) or cerium (for example $Ce_2O_3$), mixed oxides of the corresponding metals and mixtures of such oxides. The pigments are particularly preferably those based on $TiO_2$.

It is particularly advantageous for the purposes of the present invention if the inorganic pigments are present in hydrophobic form, i.e. if they have been surface-treated to repel water. This surface treatment can comprise providing the pigments with a thin hydrophobic layer by processes known per se.

Such a process comprises, for example, producing the hydrophobic surface layer by a reaction according to

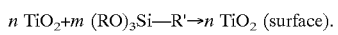

$n\ TiO_2 + m\ (RO)_3Si{-}R' \rightarrow n\ TiO_2\ (surface)$.

n and m here are stoichiometric parameters to be employed as desired and R and R' are the desired organic radicals. Hydrophobicized pigments prepared analogously to DE-A 33 14 742, for example, are advantageous.

Advantageous $TiO_2$ pigments are obtainable, for example, under the trade names MT 100 T from TAYCA.

The total amount of inorganic pigments, in particular hydrophobic inorganic micropigments, in the finished cosmetic or dermatological formulations is advantageously chosen from the range 0.1–30% by weight, preferably 0.1–10.0% by weight, in particular 0.5–6.0% by weight, based on the total weight of the formulations.

The cosmetic and/or dermatological light protection formulations according to the invention can have the customary composition and can be used for cosmetic and/or dermatological light protection, and furthermore for the treatment, care and cleansing of the skin and/or hair and as a make-up product in decorative cosmetics.

For use, the cosmetic and dermatological formulations according to the invention are applied to the skin and/or hair in an adequate amount in the manner customary for cosmetics.

Particularly preferred cosmetic and dermatological formulations are those which are in the form of a sunscreen composition. These can advantageously additionally comprise at least one further UVA filter and/or at least one further UVB filter and/or at least one inorganic pigment, preferably an inorganic micropigment.

The cosmetic and dermatological formulations according to the invention can comprise cosmetic auxiliaries such as are usually used in such formulations, for example preservatives, bactericides, perfumes, antifoams, dyes, pigments which have a colouring action, thickeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

An additional content of antioxidants is generally preferred. According to the invention, favourable antioxidants which can be used are all the antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones, penta-, hexa- and heptathionine-sulphoximine) in very low tolerated doses (for example pmol to μmol/kg), and furthermore (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, transstilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the formulations is preferably from 0.001 to 30% by weight, particularly preferably 0.05–20% by weight, in particular 1–10% by weight, based on the total weight of the formulation.

If vitamin E and/or derivatives thereof is or are the antioxidant or antioxidants, it is advantageous to choose the respective concentrations thereof from the range 0.001–10% by weight, based on the total weight of the formulation.

If vitamin A or vitamin A derivatives or carotenes or derivatives thereof is or are the antioxidant or antioxidants, it is advantageous to choose the respective concentrations thereof from the range 0.001–10% by weight, based on the total weight of the formulation.

The lipid phase can advantageously be chosen from the following group of substances:

mineral oils, mineral waxes oils, such as triglycerides of capric or of caprylic acid, but preferably castor oil;

fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids;

alkyl benzoates;

silicone oils, such as dimethylpolysiloxanes, diethylpolysiloxanes, diphenylpolysiloxanes and mixed forms thereof.

If appropriate, the aqueous phase of the formulations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of Carbopols, for example Carbopols of types 980, 981, 1382, 2984 and 5984, in each case individually or in combination.

It is advantageous according to the invention to employ, in addition to the combinations according to the invention, further oil-soluble UVA filters and/or UVB filters in the lipid phase and/or further water-soluble UVA filters and/or UVB filters in the aqueous phase.

The light protection formulations according to the invention can advantageously comprise further substances which absorb UV radiation in the UVB region, the total amount of filter substances being, for example, from 0.1% by weight to 30% by weight, preferably from 0.5 to 10% by weight, in particular from 1 to 6% by weight, based on the total weight of the formulations, in order to provide cosmetic formulations which protect the skin from the entire region of ultraviolet radiation. They can also be used as sunscreen compositions.

The further UVB filters can be oil-soluble or water-soluble. Advantageous oil-soluble UVB filter substances are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)benzoate and amyl 4-(dimethylamino)benzoate;

esters of cinnamic acid, preferably 2-ethylhexyl 4-methoxycinnamate and isopentyl 4-methoxycinnamate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate.

Advantageous water-soluble UVB filter substances are, for example:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and salts thereof;

sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)benzenesulphonic acid and salts thereof.

The list of UVB filters mentioned which can be used in combination with the active ingredient combinations according to the invention is not of course intended to be limiting.

It may also be advantageous to combine the combinations according to the invention with UVA filters which have hitherto customarily been present in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. These combinations and formulations which comprise these combinations are also provided by the invention. The amounts used for the UVB combination can be employed.

It is furthermore advantageous to combine the active ingredient combinations according to the invention with further UVA and/or UVB filters, for example certain salicylic acid derivatives, such as

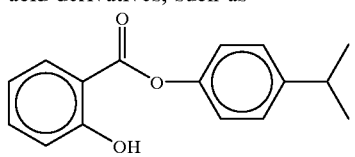

(4-isopropyl benzylsalicylate)

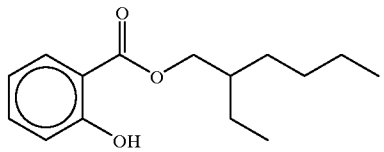

(2-ethylhexyl salicylate, octyl salicylate)

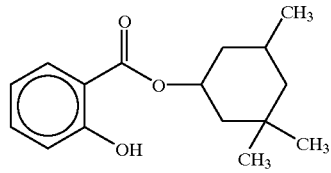

(homomenthyl salicylate).

The total amount of one or more salicylic acid derivatives in the finished cosmetic or dermatological formulations is advantageously chosen from the range 0.1–15.0% by weight, preferably 0.5–8.0% by weight, based on the total weight of the formulations. If ethylhexyl salicylate is chosen, it is advantageous to choose the total amount thereof from the range 0.1–5.0% by weight, preferably 0.5–2.5% by weight. If homomenthyl salicylate is chosen, it is advantageous to choose the total weight thereof from the range 0.1–10.0% by weight, preferably 0.5–5.0% by weight.

The example below serves to illustrate the present invention without limiting it. Unless stated otherwise, all quantities, proportions and percentages are by weight and based on the total amount or on the total weight of the formulations.

EXAMPLE 1

|  | % by weight |
|---|---|
| Glyceryl anolate | 1.00 |
| Wool wax alcohol | 0.10 |
| Polyglyceryl-2 polyhydroxystearate | 5.00 |
| Paraffin oil (paraffinum liquidum) | 6.00 |
| Isohexadecane | 4.00 |
| Myristyl myristate | 3.00 |
| Butylmethoxydibenzoylmethane | 2.00 |
| Methylbenzylidenecamphor | 4.00 |
| Octyltriazone (Uvinul T150) | 1.50 |
| Titanium dioxide | 2.00 |
| Lactic acid | 1.00 |
| NaOH | q.s. |
| Glycerol | 5.00 |
| Ethanol | 2.00 |
| MgSO$_4$ | 0.70 |
| Bisabolol | 0.10 |
| Na$_3$HEDTA | 0.50 |
| Tocopheryl acetate | 0.50 |
| Water | ad 100.00 |

We claim:

1. Cosmetic or dermatological light protection formulations in the form of W/O emulsions, comprising (a) one or more light protection filter substances which are solid under normal conditions and (b) one or more W/O emulsifiers selected from the group consisting of substances of the structural formula

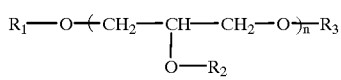

in which $R_1$, $R_2$ and $R_3$ independently of one another are selected from the group consisting of: H, branched or unbranched, saturated or unsaturated fatty acid radicals having from 8 to 24 carbon atoms, in which up to 3 aliphatic hydrogen atoms may be substituted by hydroxyl groups, and n is a number from 2 to 8.

2. Light protection formulations according to claim 1, wherein said light protection filter substances are selected from the group consisting of tris(2-ethylhexyl) 4,4',4"-(1,3,5-triazine-2,4,6-triyltriimino)trisbenzoate, 4-methylbenzylidenecamphor, 4-(tert-butyl)-4'-methoxydibenzoylmethane, and inorganic micropigments.

3. Light protection formulations according to claim 2, wherein said inorganic micropigments are selected from the group consisting of hydrophobicized inorganic micropigments.

4. Light protection formulations according to claim 3, wherein said hydrophobicized inorganic micropigment is hydrophobicized titanium dioxide.

5. Light protection formulations according to claim 1, wherein said W/O emulsifier is polyglyceryl-2 polyhydroxystearate.

6. A method of protecting skin from the damaging effects of light comprising applying to the skin a light protective effective amount of a light protective formulation according to claim 1.

7. A method of protecting hair from the damaging effects of light comprising applying to the hair a light protective effective amount of a light protective formulation according to claim 1.

* * * * *